(12) United States Patent
Lee et al.

(10) Patent No.: US 8,825,564 B2
(45) Date of Patent: Sep. 2, 2014

(54) VISUAL DRIVE CONTROL METHOD AND APPARATUS WITH MULTI PHASE ENCODING

(75) Inventors: Po-Lei Lee, Taoyuan County (TW); Kuo-Kai Shyu, Taoyuan County (TW)

(73) Assignee: National Central University, Taoyuan County (TW)

( * ) Notice: Subject to any disclaimer, the term of this patent is extended or adjusted under 35 U.S.C. 154(b) by 636 days.

(21) Appl. No.: 13/215,236

(22) Filed: Aug. 23, 2011

(65) Prior Publication Data

US 2012/0249614 A1  Oct. 4, 2012

(30) Foreign Application Priority Data

Mar. 30, 2011  (TW) .............................. 100111052 A

(51) Int. Cl.
G06F 15/18 (2006.01)
A61B 5/0482 (2006.01)
G06F 3/01 (2006.01)

(52) U.S. Cl.
CPC .............. *A61B 5/0482* (2013.01); *G06F 3/015* (2013.01)
USPC ........................................................ 706/12

(58) Field of Classification Search
CPC combination set(s) only.
See application file for complete search history.

(56) References Cited

U.S. PATENT DOCUMENTS

| 4,822,162 | A | 4/1989 | Richardson | |
| 4,926,969 | A | 5/1990 | Wright et al. | |
| 7,323,964 | B1 * | 1/2008 | Shyu et al. | 336/131 |
| 7,338,171 | B2 * | 3/2008 | Hsieh et al. | 351/237 |
| 7,541,847 | B2 * | 6/2009 | Shyu et al. | 327/108 |
| 8,648,800 | B2 * | 2/2014 | Lee et al. | 345/156 |

FOREIGN PATENT DOCUMENTS

| CN | 101328062 A | 12/2008 |
| TW | 591481 | 6/2004 |
| TW | 200945042 | 11/2009 |
| WO | 2009135092 A2 | 11/2009 |

* cited by examiner

*Primary Examiner* — Michael B Holmes
(74) *Attorney, Agent, or Firm* — CKC & Partners Co., Ltd.

(57) ABSTRACT

A visual drive control method with multi-phase encoding includes the following steps. A plurality of flickering sequences are generated by an encoding process according to a reference phase and a plurality of shifting phases divided in time division under at least one phase shift state, then a display unit is driven to display corresponding optical images. An optic nerve of an organism is evoked by the optical images, such that the organism generates a corresponding biological signal. Next, a computation process is performed to a digital biological signal converted from the biological signal to acquire an average captured reference phase and an average captured shifting phase of the digital biological signal. Then, the frequencies and the phase states of the digital biological signal and the flickering sequences are compared to output a corresponding control signal. A visual drive control apparatus with multi-phase encoding is disclosed herein.

14 Claims, 5 Drawing Sheets

VISUAL DRIVE CONTROL METHOD AND APPARATUS WITH MULTI PHASE ENCODING

RELATED APPLICATIONS

This application claims priority to Taiwan Patent Application Serial Number 100111052, filed Mar. 30, 2011, which is herein incorporated by reference.

BACKGROUND

1. Technical Field

The present disclosure relates generally to a visual drive control method and apparatus, and more particularly to a visual drive control method and apparatus with multi-phase encoding.

2. Description of Related Art

In the past decades, brain computer interface (BCI) systems with steady-state visual evoked potential (SSVEP) are developed and utilized in the biomedical field, and they are also utilized widely to control the driving control interface of the specific devices for people unable to move freely. A frequency-tagged signal and/or a phase-tagged signal are adopted as a signal source of a flicker displaying device, used as visual targets, for the steady-state visual evoked potential method.

When the steady-state visual evoked potential method with the frequency-tagged signal is adopted in the brain computer interface system, optic nerve of an organism is evoked by the visual targets, which have different frequencies, in order to generate brain wave signals related to the frequencies of the visual targets. However, the visual targets under several different frequencies will cause the visual display to be messy, and tend to cause the visual fatigue for the user.

On the other hand, when the steady-state visual evoked potential method with the phase-tagged signal is adopted in the brain computer interface system, the optic nerve of the organism is evoked by the visual targets, which have different phases, in order to generate the brain wave signals related to the phases of the visual targets. The visual display is less messy due to the visual targets have the same frequency, and has the advantage of less visual fatigue for viewers. However, a calibration process has to be performed to the phases of the visual targets and the phases of the brain wave signals to find out a specific reference phase of the brain wave signals for each user before using the brain computer interface system with phase-tagged signal. Because the user adaptations of the visual targets are not the same, a phase shift is generated in the reference phase of the brain wave signal of the user after a long term of visual stimulation, such that the phase shift between the phases of the visual targets and the phases of the brain wave signals has to be calibrated frequently in the brain computer interface system with phase-tagged signal to acquire a correct correlation between the phases of the brain wave signals and the phases of the visual targets.

Therefore, the brain computer interface systems have less visual fatigue to the user, but it cause the inconvenience of operating the brain computer interface systems with phase calibration process which has to be improved necessarily.

SUMMARY

One aspect of the present disclosure is to provide a visual drive control method with multi-phase encoding to solve the inconvenience of phase calibration in operating the brain computer interface system with phase-tagged steady-state visual evoke potential.

The visual drive control method with multi-phase encoding includes the following steps. A plurality of flickering sequences are generated by an encoding process according to a reference phase and a plurality of shifting phases divided in time under at least one phase shift state. A display unit is driven by the flickering sequences to display a plurality of optical images corresponding to the flickering sequences. Then, optic nerve of an organism is evoked by the optical images such that a biological signal corresponding to the optical image is generated by the organism. After that, the biological signal is converted to a digital biological signal. Next, a computation process is performed to the digital biological signal to acquire an average captured reference phase corresponding to the reference phase, of the digital biological signal, and to acquire an average captured shifting phase corresponding to one of the shifting phases, of the digital biological signal. Afterward, frequencies and phase states of the digital biological signal and the flickering sequences are compared to output a corresponding control signal.

According to one embodiment of the present disclosure, comparing the frequencies and phase states of the digital biological signal and flickering sequences further includes the following steps. The frequencies of the digital biological signal are compared with the frequencies of the flickering sequences. A phase difference between the average captured reference phase and the average captured shifting phase is calculated to acquire an average phase difference when the frequencies of the digital biological signal and the frequencies of the flickering sequences are conformed. Then, the average phase difference is compared with the shifting phases to output the corresponding control signal.

According to one embodiment of the present disclosure, at least one of the flickering sequences is operated under a reference phase state and a plurality of phase shift states sequentially in time, and the flickering sequences have different shifting phases under the phase shift states.

According to one embodiment of the present disclosure, the visual drive control method further includes using a plurality of frequencies to encode the flickering sequences with multi-phase encoding to extend the available number of control outputs.

According to one embodiment of the present disclosure, at least one of the flickering sequences is operated under a reference phase state and a plurality of phase shift states sequentially in time, and the flickering sequences have different shifting phases and a plurality of different frequencies under the phase shift states.

According to one embodiment of the present disclosure, the frequencies of the flickering sequences are fixed or adjustable.

According to one embodiment of the present disclosure, a time period of the flickering sequences operated under a reference phase state and the phase shift states is fixed or adjustable.

Another aspect of the present disclosure is to provide a visual drive control apparatus with multi-phase encoding to solve the inconvenience of operating the brain computer interface system with phase-tagged steady-state visual evoke potential.

The visual drive control apparatus with multi-phase encoding includes a flicker generating unit, a display unit, a biological signal measuring unit, and a signal processing unit. The flicker generating unit is used for generating a plurality of flickering sequences by an encoding process according to a reference phase and a plurality of shifting phases divided in time under at least one phase shift state. The display unit is electrically coupled to the flicker generating unit, for displaying a plurality of optical images corresponding to the flickering sequences. The biological signal measuring unit is connected to an organism, for acquiring a biological signal of the organism. The biological signal is generated by optical nerve of the organism evoked by the optical images. The signal processing unit is electrically coupled to the biological signal measuring unit, for performing a signal processing procedure to the biological signal to output a corresponding control signal.

According to one embodiment of the present disclosure, the signal processing unit further includes a biological signal amplifier, an A/D converter, and a processor. The biological signal amplifier is electrically coupled to the biological signal measuring unit, for amplifying the biological signal acquired by the biological signal measuring unit. The A/D converter is electrically coupled to the biological signal amplifier, for converting the biological signal to a digital biological signal. The processor is electrically coupled to the A/D converter and the flicker generating unit, for performing a computation process to the digital biological signal to acquire an average captured reference phase corresponding to the reference phase, of the digital biological signal, and to acquire an average captured shifting phase corresponding to one of the shifting phases, of the digital biological signal, and for comparing frequencies and phase states of the digital biological signal and the flickering sequences to output the corresponding control signal.

According to one embodiment of the present disclosure, the optical images are formed by a pure light or an adjustable brightness pattern respectively.

According to one embodiment of the present disclosure, the display unit has a plurality of optical devices, the optical devices have fixed or adjustable flicker cycles.

According to one embodiment of the present disclosure, the flickering sequences are generated by a programmable chip including single chip processor, FPGA or micro-controller.

According to one embodiment of the present disclosure, the biological signal measuring unit is used for acquiring the biological signal of the organism by attaching at least one electrode on the brain visual area, attaching a reference electrode on the post auricular mastoid and attaching a ground electrode on the forehead of the organism in accordance with standard 10-20 system.

According to one embodiment of the present disclosure, the visual drive control apparatus with multi-phase encoding further includes a control unit electrically coupled to the signal processing unit, for receiving the control signal to control peripheral equipments and to perform a corresponding action.

It is to be understood that both the foregoing general description and the following detailed description are by examples, and are intended to provide further explanation of the invention as claimed.

DETAILED DESCRIPTION

Figure 1:
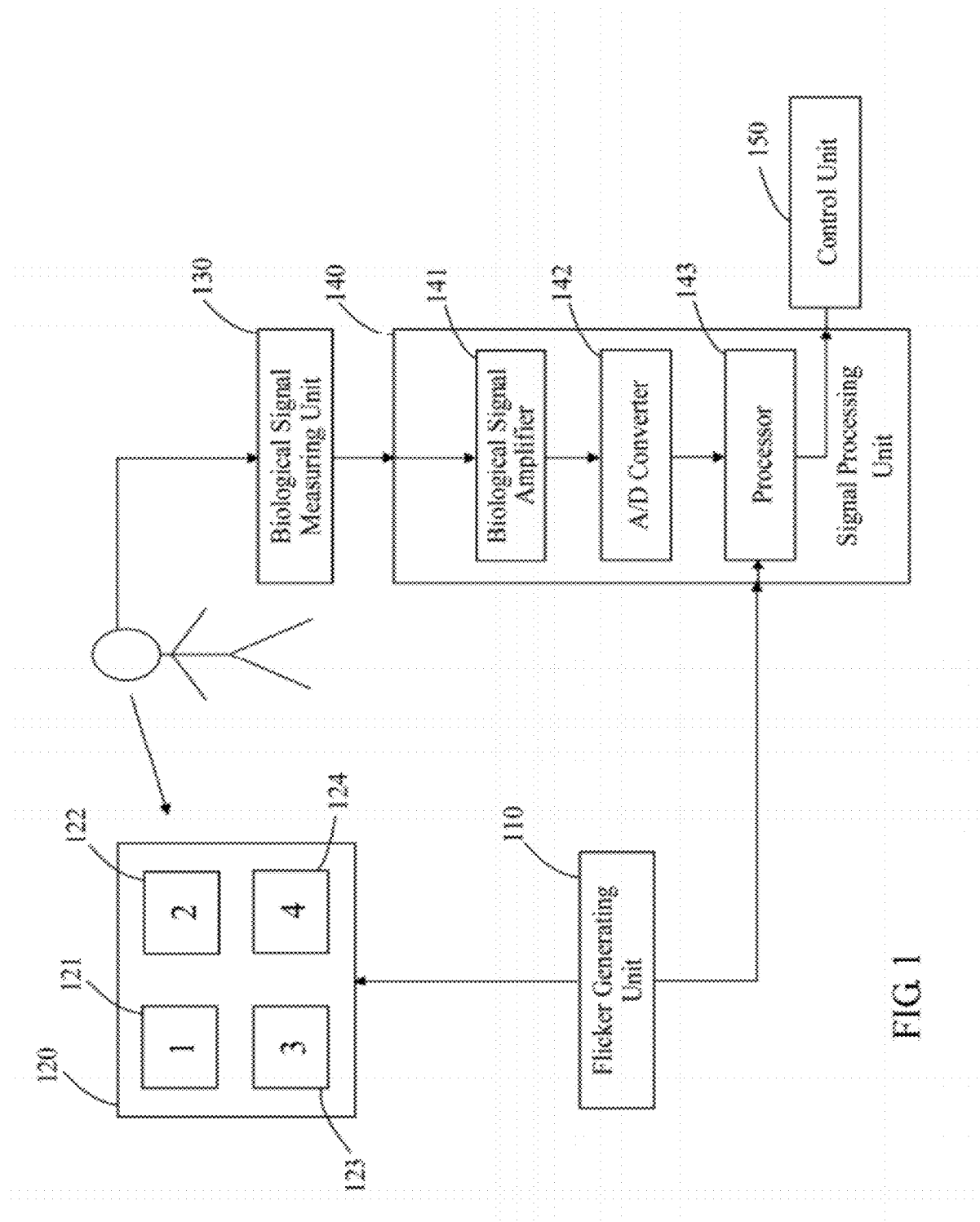
FIG. 1 shows a block diagram of the visual drive control apparatus with multi-phase encoding according to one embodiment of the present disclosure.

Reference will now be made in detail to the present embodiments of the invention, examples of which are illustrated in the accompanying drawings. Wherever possible, the same reference numbers are used in the drawings and the description to refer to the same or like parts.

FIG. 1 shows a block diagram of the visual drive control apparatus with multi-phase encoding according to one embodiment of the present disclosure.

The visual drive control apparatus with multi-phase encoding includes a flicker generating unit 110, a display unit 120, a biological signal measuring unit 130, and a signal processing unit 140. The flicker generating unit 110 is used for generating a plurality of flickering sequences by an encoding process according to a reference phase and a plurality of shifting phases divided in time under at least one phase shift state. The display unit 120 is electrically coupled to the flicker generating unit 110 to display a plurality of optical images corresponding to the flickering sequences. The biological signal measuring unit 130 is connected to an organism to acquire a biological signal of the organism, in which the biological signal is generated by optic nerve of the organism evoked by the optical images. The signal processing unit 140 is electrically coupled to the biological signal measuring unit 130 to perform a signal processing procedure to the biological signal to output a corresponding control signal.

In one embodiment of the present disclosure, the signal processing unit 140 further includes a biological signal amplifier 141, an A/D converter 142, and a processor 143. The biological signal amplifier 141 is electrically coupled to the biological signal measuring unit 130 to amplify the biological signal acquired by the biological signal measuring unit 130. The A/D converter 142 is electrically coupled to the biological signal amplifier 141 to convert the biological signal to a digital biological signal. The processor 143 is electrically coupled to the A/D converter 142 and the flicker generating unit 110 to perform a computation process to the digital biological signal to acquire an average captured reference phase corresponding to the reference phase, of the digital biological signal, and to acquire an average captured shifting phase corresponding to one of the shifting phases, of the digital biological signal, and to compare frequencies and phase states of the digital biological signal and the flickering sequences to output the corresponding control signal.

In one embodiment of the present disclosure, the flickering sequences can be generated by a programmable chip. The programmable chip at least includes a single chip processor, FPGA or micro-controller. The flickering sequences can drive the display unit 120 including a first optical device 121, a second optical device 122, a third optical device 123, and a fourth optical device 124 to generate a first optical image, a second optical image, a third optical image, and a fourth optical image which are corresponding to the flickering sequences.

In one embodiment of the present disclosure, the visual drive control apparatus with multi-phase encoding further includes a control unit 150. The control unit 150 is electrically coupled to the processor 143 of the signal processing unit 140. The control unit 150 is used to receive the control signal to control peripheral equipments and to perform a corresponding action.

Furthermore, the signal processing unit 140 can further include a filter unit (not shown), in which a circuit type of the filter unit can be an analog filter or a digital filter. The filter unit can be electrically coupled between the biological signal amplifier 141 and the A/D converter 142, or electrically coupled between the A/D converter 142 and the processor 143 according to a circuit design type of the filter unit. The filter unit is used to filter out the noise being outside of the frequency ranges (e.g. 27 Hz to 36 Hz) of the flickering sequences to increase the signal to noise ratio, in order to perform the computation process to the digital biological signal by the processor 143. The foregoing noise includes heart beat frequency, biological noise of the organism, power noise and other external noises. It is noted that the circuit design type and the placement of the foregoing filter unit are not intended to limit the scope of the present disclosure.

In operation, the biological signal measuring unit 130 can be used to acquire the biological signal of the organism by attaching at least one electrode on the brain visual area, attaching a reference electrode on the post auricular mastoid and attaching a ground electrode on the forehead of the organism in accordance with standard 10-20 system. Specifically, when a user (or the organism) is watching the optical images (e.g. four optical images which are generated from the first optical device 121 to the fourth optical device 124) generated by the display unit 120, the brain wave signal generated by the optic nerve of the user is acquired by the electrode, reference electrode and ground electrode of the biological signal measuring unit 130, in which the brain wave signal (or biological signal) is generated by the optic nerve of the user evoked by the optical images. Then, the biological signal measuring unit 130 transmits the brain wave signal to the signal processing unit 140, and the biological signal amplifier 141 amplifies the brain wave signal to enlarge the amplitude of the brain wave signal. After that, the brain wave signal is converted to the digital brain wave signal (or the digital biological signal) by the A/D converter 142.

Figure 2:
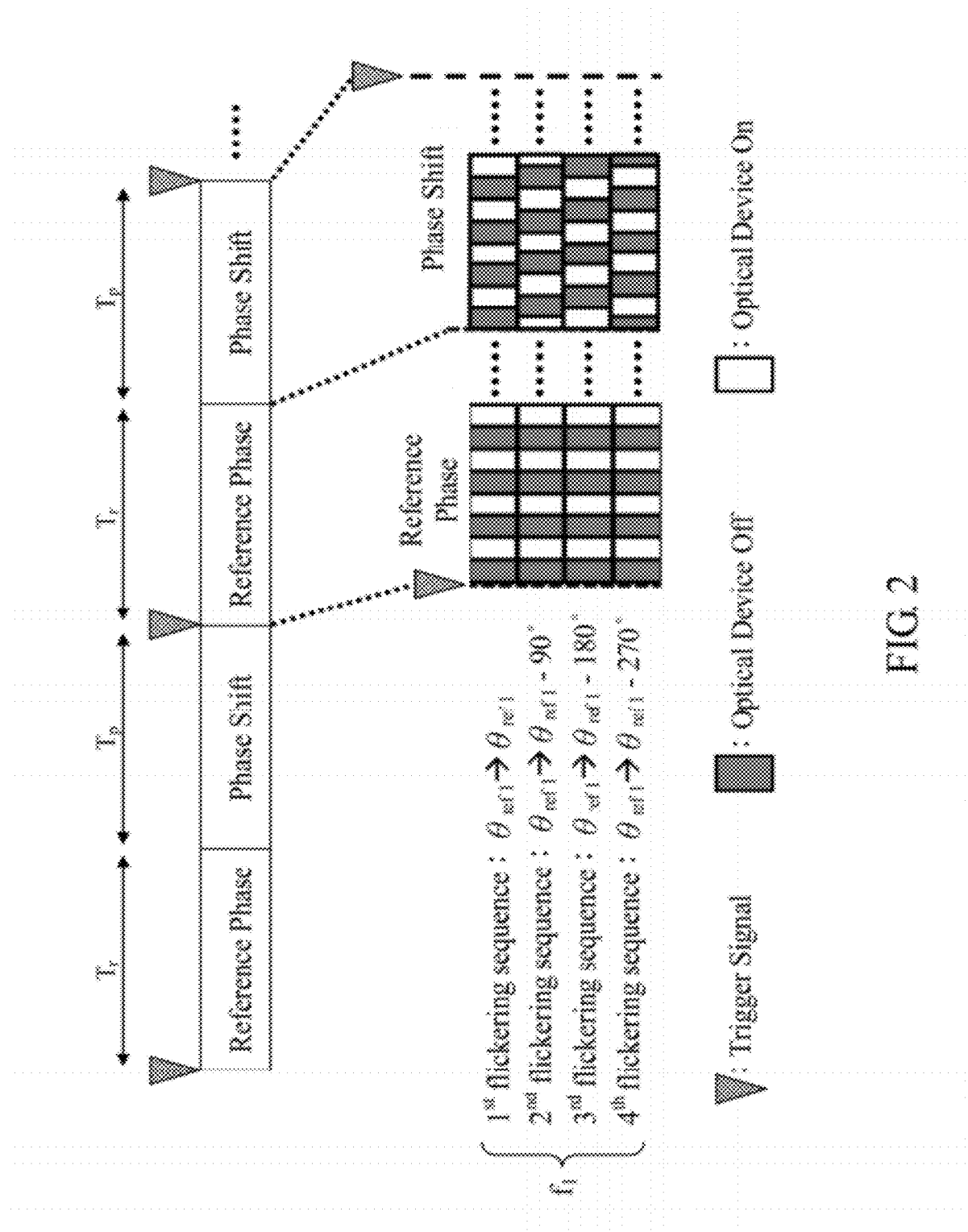
FIG. 2 shows a functional diagram of the flickering sequences generated by the visual drive control method with multi-phase encoding according to one embodiment of the present disclosure.

According to the foregoing description, the flickering sequences are generated from the flicker generating unit 110 by the encoding process according to the reference phase and the shifting phases divided in time under at least one phase shift state. For example, the flickering sequences can be generated by the flicker generating unit 110 according to the encoding method as shown in FIG. 2. FIG. 2 shows a diagram of the flickering sequences generated by the visual drive control method with multi-phase encoding according to one embodiment of the present disclosure.

Please refer to FIG. 1 and FIG. 2 at the same time. In the present embodiment, an encoding method with dual-phase stimulation is provided. Namely, in this encoding method, the flickering sequences are composed under one reference phase state and one phase shift state with a first frequency (e.g. $f_1=31.25$ Hz). Then the reference phase state is connected in series with different shifting phases of the phase shift state to form an encoding combination as $\theta_{ref1} \to \phi$. In one embodiment, the shifting phase of 90° is adopted, and the period of 360° is divided into four parts by the shifting phase of 90°, i.e. $\theta_{ref1} \to \theta_{ref1}$, $\theta_{ref1} \to \theta_{ref1}-90°$, $\theta_{ref1} \to \theta_{ref1}-180°$, and $\theta_{ref1} \to \theta_{ref1}-270°$, as four encoding combinations. Therefore, there are four flickering sequences having dual-phase states (e.g. from the 1st flickering sequence to the 4th flickering sequence) can be generated under one flickering frequency $f_1$. If two flickering frequencies (e.g. the first frequency $f_1=31.25$ Hz and the second frequency $f_2=36$ Hz) are adopted, there are eight flickering sequences having dual-phase states can be generated.

In one embodiment of the present disclosure, the frequencies that are used for the flickering sequences with multi-phase can be fixed or adjustable. For example, the first frequency can be set to 31.25 Hz or set within a specific frequency range of from 27 Hz to 36 Hz. Further, a time period of the reference phase state ($T_r$) and a time period of the phase shift state ($T_p$) can be fixed or adjustable. For example, the time period of the reference phase state can be set to be the duration of 0~0.9 second after a trigger signal, and the time period of the phase shift state can be set to be the duration of 0.9~1.8 second after the trigger signal. Moreover, when the reference phase (or the shifting phase) acquired from the brain wave signal of the user is stable, the flickering sequences are permitted to translate to the next phase state so as to display the corresponding optical images. Consequently, the time period (or duration) of the reference phase state and the phase shift state are adjustable and not intended to limit the scope of the present disclosure.

In another embodiment of the present disclosure, the optical images may be formed by a pure light or an adjustable brightness pattern respectively. For example, the optical devices of the display unit 120 may include luminous elements, such as LED, LCD and lamp, to generate the optical images having only bright or dark, or to generate the optical images with adjustable brightness and/or with different color outputs, by a controlling circuit, in which flicker cycles of the optical images are fixed or adjustable to achieve a comfortable visual display and an actual requirement in application. For example, for the flickering frequency in which the first frequency is 31.25 Hz, each flicker cycle of the flickering sequence is 32 millisecond (ms). The user can choose a flickering manner with a duty cycle of a half bright (16 ms)/half dark (16 ms), or choose another flickering manner with a duty cycle of 24 ms in bright and 8 ms in dark. As long as the combination of the bright period and the dark period is 32 ms in each flicker cycle, the combination belongs to the same display manner with the first frequency of 31.25 Hz.

Therefore, all of the frequencies, number of optical images, phase time periods, and the flickering manner and the flicker cycles of the flickering sequences are adjustable in actual application or in operation to generate the optical images, and it is not intended to limit the scope of the present disclosure.

Figure 3:
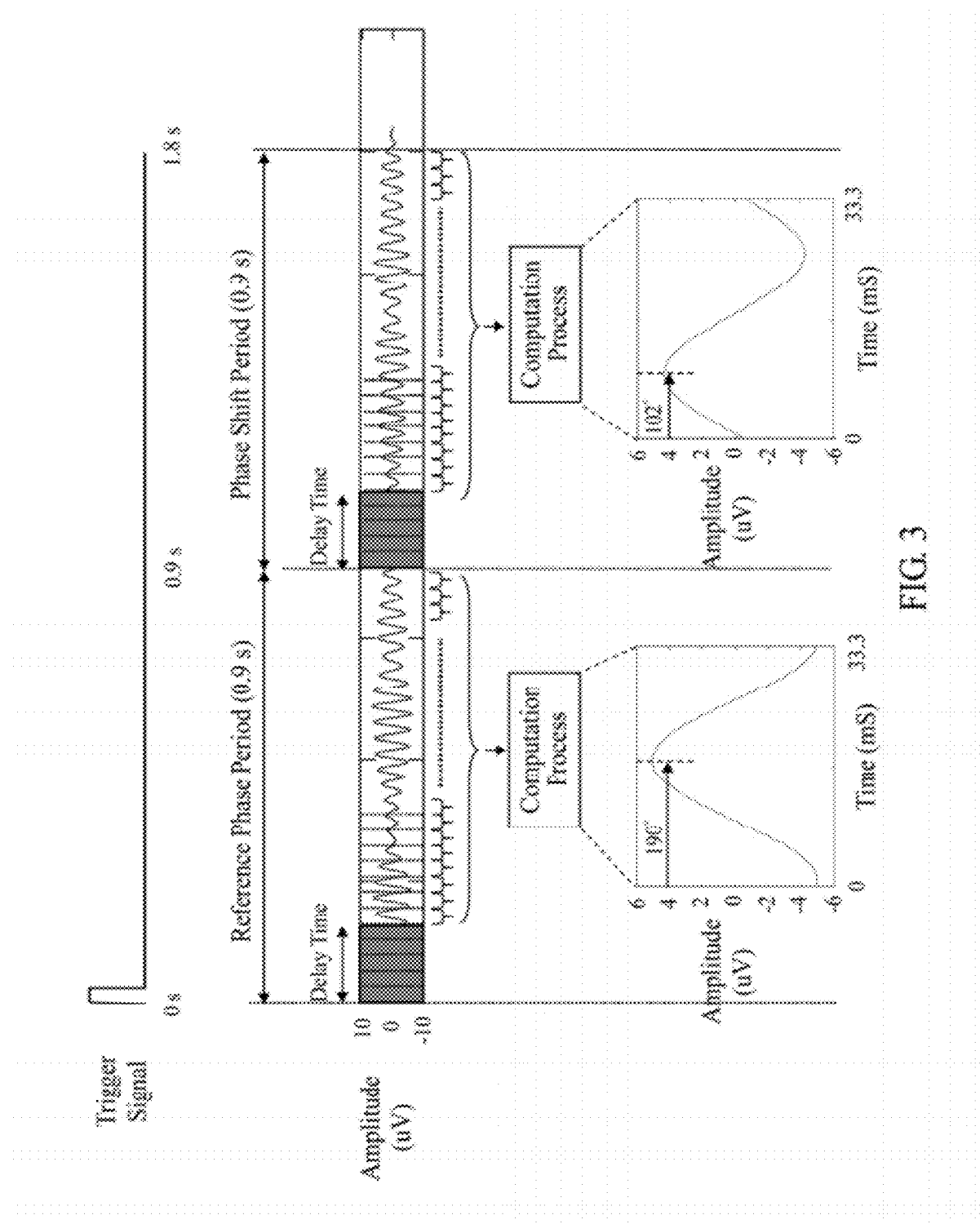
FIG. 3 shows a functional diagram relating to perform a computation process to the biological signal by the visual drive control method with multi-phase encoding according to one embodiment of the present disclosure.

FIG. 3 shows a diagram of performing a computation process to the biological signal of the visual drive control method with multi-phase encoding according to one embodiment of the present disclosure. Please refer to FIG. 1, FIG. 2, and FIG. 3 at the same time. The processor 143 performs the computation process, such as Fourier Transform, time average or wavelet analysis to the digital brain wave signal to acquire the average captured reference phase and the average captured shifting phase, of the digital brain wave signal. For example, the average captured reference phase, of the digital brain wave signal, is 190°, and the average captured shifting phase, of the digital brain wave signal, is 102°. The processor 143 compares the frequencies of the digital brain wave signal with the frequencies of the flickering sequences. When the frequencies of the digital brain wave signal and the frequencies of the flickering sequences are conformed (e.g. the frequencies of the digital brain wave signal and the flickering sequences are 31.25 Hz), it is meant that the brain wave signal is evoked in accordance with the optical devices of the display unit 120. Then, the average phase difference between the average captured reference phase and the average captured shifting phase is calculated to be 88°. After that, the average phase difference is compared with the shifting phases of the flickering sequences to find out the correlation. Thus, it can be seen that the average phase difference is corresponding to the second flickering sequence which has a shifting phase of 90°, and it can be inferred that the user is watching the second optical device 122. Next, the processor 143 generates the control signal corresponding to the second flickering sequence.

After the control unit 150 receives the control signal, the control unit 150 controls the peripheral equipments to perform the corresponding action in accordance with the control signal. For example, the forward, rightward, backward and leftward movement of a wheelchair can be controlled and the movement of the wheelchair is corresponding to the first flickering sequence to the fourth flickering sequence. After the computation and comparing process is performed to the digital biological signal and the flickering sequences, it can be seen that the digital biological signal is corresponding to the second flickering sequence. Therefore, the processor 143 outputs the control signal corresponding to the second flickering sequence to the control unit 150 to drive the wheelchair for making the rightward movement.

Figure 4:
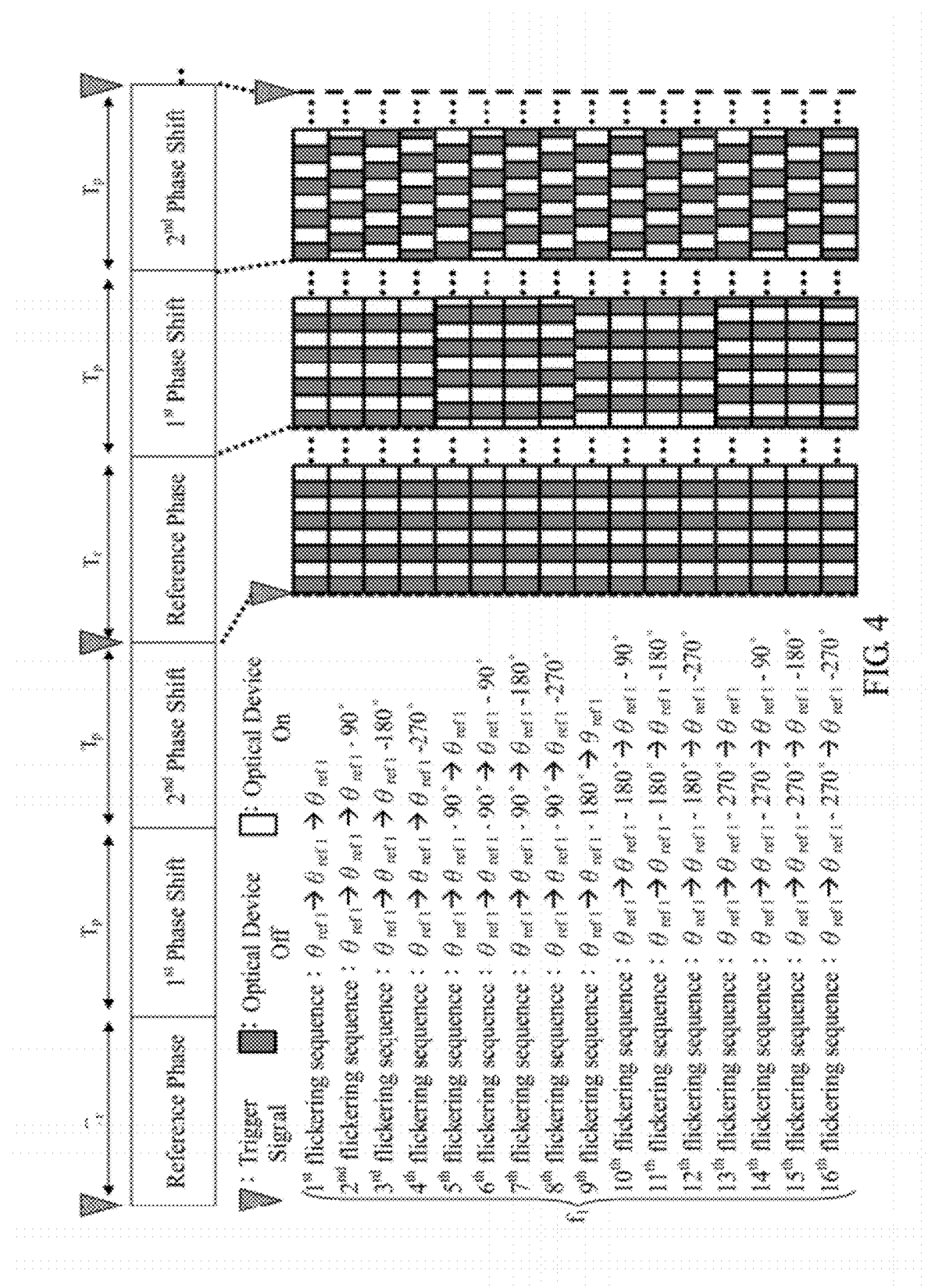
FIG. 4 shows a functional diagram of the flickering sequences generated by the visual drive control method with multi-phase encoding according to one embodiment of the present disclosure.

FIG. 4 shows a functional diagram of the flickering sequences generated by the visual drive control method with multi-phase encoding according to the second embodiment of the present disclosure. One of the flickering sequences is operated under one reference phase and a plurality of phase shift states sequentially in time, and the flickering sequences have different shifting phases under the phase shift states. For example, the flickering sequences are generated by the flicker generating unit 110 in accordance with the encoding method as shown in FIG. 4.

Please refer to FIG. 1 and FIG. 4 at the same time. The encoding method with triple-phase stimulation is provided in this example of the present disclosure. Namely, the flickering sequences are composed under one reference phase state and two phase shift states (e.g. a first phase shift state and a second phase shift state) with the first frequency (e.g. $f_1$=31.25 Hz). Then, one reference phase state is connected in series with different shifting phases, such as the first phase shift state and the second phase shift state to form an encoded combination as $\theta_{ref1} \to \phi_1 \to \phi_2$. In one embodiment, the shifting phase of 90° is adopted, and the period of 360° is divided into four parts by the shifting phase of 90°, i.e. $\theta_{ref1} \to \theta_{ref1} \to \theta_{ref1}$, $\theta_{ref1} \to \theta_{ref1} \to \theta_{ref1}-90°$, $\theta_{ref1} \to \theta_{ref1} \to \theta_{ref1}-180°$, $\theta_{ref1} \to \theta_{ref1} \to \theta_{ref1}-270°$, $\theta_{ref1} \to \theta_{ref1}-90° \to \theta_{ref1}$, $\theta_{ref1} \to \theta_{ref1}-90° \to \theta_{ref1}-90°$, $\theta_{ref1} \to \theta_{ref1}-90°$, $\theta_{ref1} \to \theta_{ref1}-180°$, $\theta_{ref1} \to \theta_{ref1}-90° \to \theta_{ref1}-270°$, ..., $\theta_{ref1} \to \theta_{ref1}-270° \to \theta_{ref1}-270°$, as 16 combinations. Therefore, these 16 combinations with triple-phase states of flickering sequences can be generated under one flickering frequency $f_1$, in which the optical images of the flickering sequences can be displayed with the corresponding optical devices of the display unit 120.

Hence, more flickering sequences can be generated by the encoding method with one reference phase in the reference phase state and a plurality of the shifting phases in the first phase shift state and the second phase shift state. Consequently, more control signals can be obtained without increasing the device complexity and the complexity of the controlled manner, of the brain computer interface, to control precise and complex actions of the equipments or devices. For example, the actions of the robot or the robot arms can be controlled by the foregoing control signal. It is noted, beside the encoding method of the flickering sequences, the visual drive structures and the visual drive controlling methods are the same or similar as the foregoing embodiment, and without excess description herein.

Figure 5:
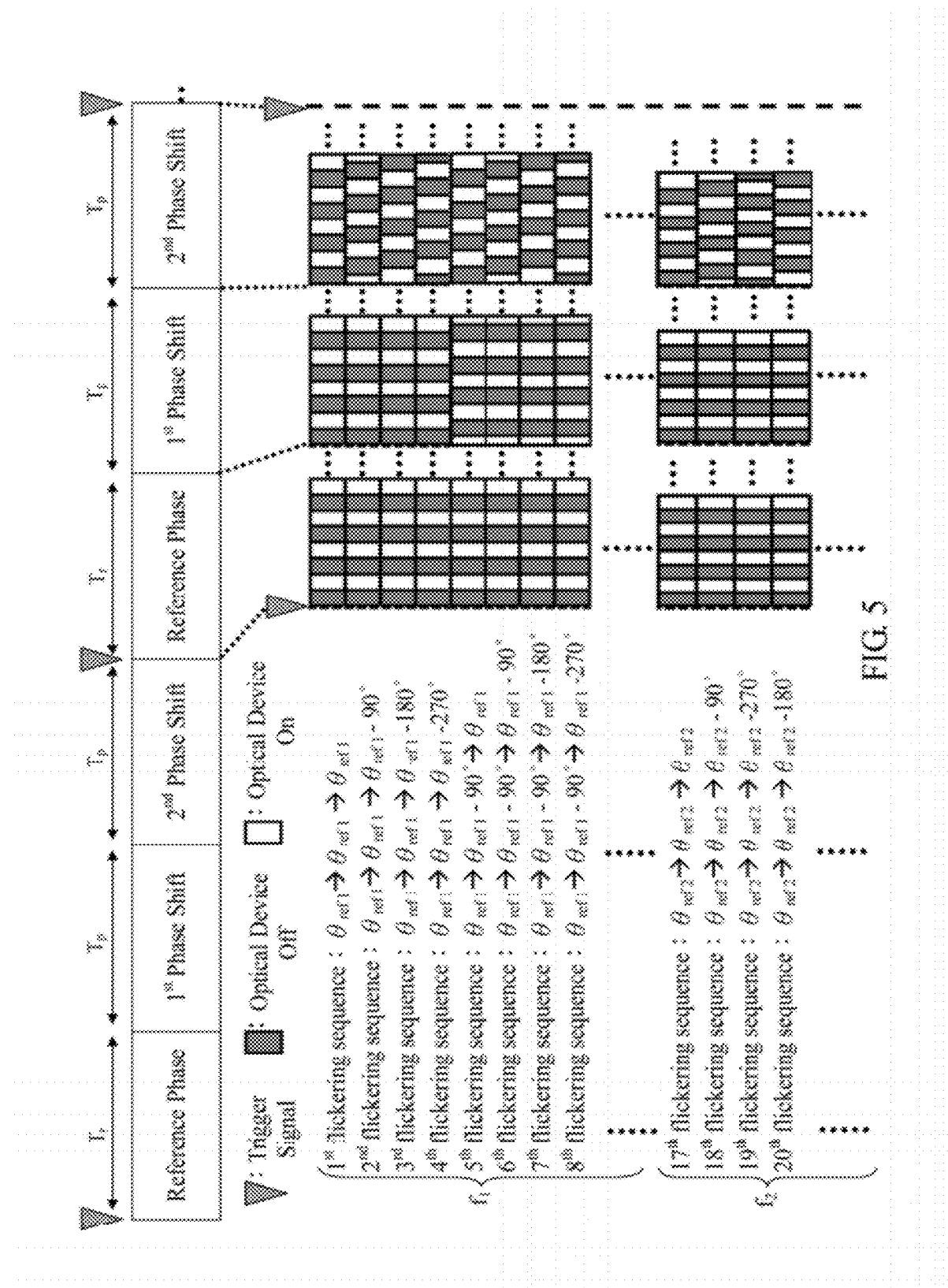
FIG. 5 shows a functional diagram of the flickering sequences generated by the visual drive control method with multi-phase encoding according to one embodiment of the present disclosure.

FIG. 5 shows a functional diagram of the flickering sequences generated by the visual drive control method with multi-phase encoding according to one embodiment of the present disclosure. The number of control outputs can be increased by applying multiple-frequency to the flickering sequences generated by the visual drive control method with multi-phase encoding. At least one of the flickering sequences is operated under one reference phase state and a plurality of phase shift states sequentially in time, and the flickering sequences have different shifting phases and a plurality of different frequencies in the phase shift states. For example, the flickering sequences can be generated by the flicker generating unit 110 in accordance with the encoding method, in which, the frequencies can be used for the flickering sequences with multi-phase encoding to extend the available number of control output, as shown in FIG. 5.

Please refer to FIG. 1 and FIG. 5 at the same time. The encoding method with dual-frequency and triple-phase stimulation is provided in this embodiment of the present disclosure. Namely, the flickering sequences are composed under one reference phase state and two phase shift states with two flickering frequencies (e.g. the first frequency $f_1$=31.25 Hz and the second frequency $f_2$=36 Hz), in this encoding method. Then, one reference phase state is connected in series with different shifting phases of the first phase shift state and the second phase shift state with the same flickering frequency, such as the first frequency, to form an encoded combinations as $\theta_{ref1} \to \phi_1 \to \phi_2$. In one embodiment, the shifting phase of 90° is adopted, and the period of 360° is divided into four parts by the shifting phase of 90°, i.e. $\theta_{ref1} \to \theta_{ref1} \to \theta_{ref1}$, $\theta_{ref1} \to \theta_{ref1} \to \theta_{ref1}-90°$, $\theta_{ref1} \to \theta_{ref1} \to \theta_{ref1}-180°$, $\theta_{ref1} \to \theta_{ref1} \to \theta_{ref1}-270°$, $\theta_{ref1} \to \theta_{ref1}-90° \to \theta_{ref1}$, $\theta_{ref1} \to \theta_{ref1}-90° \to \theta_{ref1}-90°$, $\theta_{ref1} \to \theta_{ref1}-90° \to \theta_{ref1}-180°$, $\theta_{ref1} \to \theta_{ref1}-90° \to \theta_{ref1}-270°$, ..., $\theta_{ref1} \to \theta_{ref1}-270° \to \theta_{ref1}-270°$, as 16 combinations (e.g. from the 1st flickering sequence to the 16th flickering sequence). Similarly, one reference phase state can be connected in series with different shifting phases of the first phase shift state and the second phase shift state with another flickering frequency, such as the second frequency to form another 16 combinations, i.e. $\theta_{ref2} \to \theta_{ref2} \to \theta_{ref2}$, $\theta_{ref2} \to \theta_{ref2} \to \theta_{ref2}-90°$, ..., $\theta_{ref2} \to \theta_{ref2}-90° \to \theta_{ref2}$, ... $\theta_{ref2} \to \theta_{ref2}-90° \to \theta_{ref2}-90°$, ..., $\theta_{ref2} \to \theta_{ref2}-270° \to \theta_{ref2}-270°$ (e.g. from the 17th flickering sequence to the 32nd flickering sequence). In total, there are 32 flickering sequences that can be generated by the foregoing encoding method.

Therefore, more flickering sequences can be generated by the encoding method with one reference phase in the reference phase state and a plurality of the shifting phases in the first phase shift state and the second phase shift state under a plurality of frequencies. Consequently, more control signals can be obtained without increasing the device complexity and the complexity of the controlled manner, of the brain computer interface, to control precise and complex actions of the equipments or devices. It is noted, beside the encoding method of the flickering sequences, the visual drive structures and the visual drive controlling methods are the same or similar as the foregoing embodiment, and without excess description herein.

In sum, if the shifting phases of each phase shift state can be divided into K parts, $K^2$ combinations of the flickering sequences can be formed under two phase shift states. If N types of phase shift state are adopted, $K^N$ combinations of the flickering sequences can be formed. If M types of flickering frequencies are adopted, $MK^N$ combinations of the flickering sequences can be formed.

In one embodiment, a delay time is fixed or adjustable to acquire the biological signal, when the signal processing procedure is performed to the biological signal, in order to eliminate a delay response of the brain wave signal (or biological signal) caused by the optic nerve of the organism under an exhausted situation. For example, the time period of the reference phase state can be set to be the duration of 0~0.9 second after the trigger signal, and the time period of the phase shift state can be set to be the duration of 0.9~1.8 second after the trigger signal, and the delay time can be set to 0.2 second to acquire (or capture) the brain wave signal. Namely, the time period is configured to be the duration of 0.2~0.9 second after the trigger signal to acquire the reference phase, and then the average captured reference phase can be obtained after the computation process is performed to the reference phase. Further, the time period is configured to be the duration of 1.1~1.8 second after the trigger signal to acquire the shifting phases, and then the average captured shifting phase can be obtained after the computation process is performed to the shifting phases. The foregoing delay time is adjustable in actual application to acquire the brain wave signal, and it is not intend to limit the scope of the present disclosure.

Another embodiment of the present disclosure relates to a visual drive control method with multi-phase encoding. A plurality of flickering sequences can be generated by an encoding process according to one reference phase and a plurality of shifting phases divided in time under at least one phase shift state. Then, a display unit is driven by the flickering sequences to display a plurality of optical images corresponding to the flickering sequences. After that, optic nerve of an organism is evoked by the optical images such that a biological signal corresponding to the optical image is generated by the organism. Next, the biological signal is amplified, recorded, and converted to a digital biological signal. A computation process is performed to the digital biological signal to acquire an average captured reference phase corresponding to the reference phase, of the digital biological signal, and to acquire an average captured shifting phase corresponding to one of the shifting phases, of the digital biological signal. Afterward, frequencies and phase states of the digital biological signal and the flickering sequences are compared to output a corresponding control signal.

For example, in the encoding method with dual-phase stimulation shown in FIG. 2, one reference phase state and four shifting phases divided from the period of 360° in one phase shift state are composed by the flicker generating unit 110 under the flickering frequency, such as the first frequency (e.g. $f_1$=31.25 Hz), in the encoding process to generate a first flickering sequence to a fourth flickering sequence. Then, a first optical device 121 to a fourth optical device 124 of the display unit 120 can be driven by four flickering sequences to display four different optical images corresponding to the first flickering sequence to the fourth flickering sequence.

Next, the optical images are used to evoke the optic nerve of the user (or the organism), such that the user generates the brain wave signal (or biological signal) corresponding to the frequency and the phase of one optical image. For example, when the user is watching the second optical device 122, in which the second optical image corresponding to the second flickering sequence is generated by the second optical device 122, the brain wave signal is then generated by the optic nerve of the organism evoked by the second optical image. Then, the brain wave signal of the organism can be measured by the biological signal measuring unit 130 in accordance with standard 10-20 system.

The biological signal amplifier 141 then amplifies the brain wave signal, in order to perform the computation process to the brain wave signal after the amplification process. The foregoing computation process includes the Fourier transform, time average or wavelet analysis to acquire the average captured reference phase, such as 190°, corresponding to the reference phase, of the digital brain wave signal, and the average captured shifting phase, such as 102°, corresponding to one of the shifting phases, of the digital brain wave signal.

In the next step, the frequencies of the digital biological signal are compared with the frequencies of the flickering sequences. When the frequencies of the digital brain wave signal and the frequencies of the flickering sequences are conformed (e.g. both frequencies of the brain wave signal and the flickering sequences are 31.25 Hz). It means that the brain wave signal is evoked in accordance with the optical devices of the display unit 120. Then, the average phase difference between the average captured reference phase and the average captured shifting phase is calculated to be 88°. After that, the average phase difference and the shifting phase of the flickering sequences are compared to find out the average phase difference corresponding to the second flickering sequence having the shifting phase 90°, and it can be inferred that the user is watching the second optical device 122. Next, the processor 143 generates the control signal corresponding to the second flickering sequence to control the peripheral equipments with corresponding actions.

It is understood that the present invention has the following advantages in accordance with the foregoing embodiments of the present disclosure. Less flickering frequencies are needed, and multi-channel encoding (or multiple flickering sequences) with less visual fatigue for the user can be achieved. The foregoing encoding method has the reference phase and the shifting phases simultaneously, and only has to calculate the phase difference between the reference phase and the shifting phases without further calibration process to the phases of visual targets and to the phases of the brain wave signals, and this encoding method also has less interference from the other physiological signals. A comparing process can be performed to the average phase difference and the flickering sequences to obtain the relationship rapidly, and to distinguish the biological signal rapidly. More flickering sequences can be generated without increasing the device complexity and the complexity of the controlled manner, of the brain computer interface, to control precise and complex actions of the equipments or the devices.

The drawings and descriptions in the foregoing embodiments were chosen and described in order to explain the principles of the disclosure and their practical application without detailed descriptions of the whole visual drive control method and visual drive control apparatus with multi-phase encoding. The controlling steps and structures of the present disclosure could be adjusted to fit the practical application without departing from its spirit and scope.

It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims.

What is claimed is:

1. A visual drive control method with multi-phase encoding, comprising:

generating a plurality of flickering sequences by an encoding process according to a reference phase and a plurality of shifting phases divided in time under at least one phase shift state;

driving a display unit by the flickering sequences to display a plurality of optical images corresponding to the flickering sequences;

evoking optic nerve of an organism by the optical images such that a biological signal corresponding to the optical images is generated by the organism;

converting the biological signal to a digital biological signal;

performing a computation process to the digital biological signal to acquire an average captured reference phase corresponding to the reference phase, of the digital biological signal, and to acquire an average captured shifting phase corresponding to one of the shifting phases, of the digital biological signal; and comparing frequencies and phase states of the digital biological signal and the flickering sequences to output a corresponding control signal.

2. The visual drive control method with multi-phase encoding of claim 1, wherein comparing the frequencies and the phase states of the digital biological signal and the flickering sequences further comprises:

comparing the frequencies of the digital biological signal with the frequencies of the flickering sequences;

calculating a phase difference between the average captured reference phase and the average captured shifting phase to acquire an average phase difference when the frequencies of the digital biological signal and the frequencies of one of the flickering sequences are conformed; and comparing the average phase difference with the shifting phases to output the corresponding control signal.

3. The visual drive control method with multi-phase encoding of claim 1, wherein at least one of the flickering sequences is operated under a reference phase state and a plurality of phase shift states sequentially in time, and the flickering sequences have different shifting phases under the phase shift states.

4. The visual drive control method with multi-phase encoding of claim 1, further comprising:

extending the available number of control outputs by using a plurality of frequencies to encode the flickering sequences with multi-phase encoding.

5. The visual drive control method with multi-phase encoding of claim 1, wherein at least one of the flickering sequences is operated under a reference phase state and a plurality of phase shift states sequentially in time, and the flickering sequences have different shifting phases and a plurality of different frequencies under the phase shift states.

6. The visual drive control method with multi-phase encoding of claim 1, wherein the frequencies of the flickering sequences are fixed or adjustable.

7. The visual drive control method with multi-phase encoding of claim 1, wherein a time period of the flickering sequences operated under a reference phase state and the phase shift states is fixed or adjustable.

8. A visual drive control apparatus with multi-phase encoding, comprising:

a flicker generating unit for generating a plurality of flickering sequences by an encoding process according to a reference phase and a plurality of shifting phases divided in time under at least one phase shift state;

a display unit electrically coupled to the flicker generating unit, for displaying a plurality of optical images corresponding to the flickering sequences;

a biological signal measuring unit connected to an organism, for acquiring a biological signal of the organism, wherein the biological signal is generated by optic nerve of the organism evoked by the optical images; and a signal processing unit electrically coupled to the biological signal measuring unit, for performing a signal processing procedure to the biological signal to output a corresponding control signal.

9. The visual drive control apparatus with and multi-phase encoding of claim 8, wherein the signal processing unit comprises:

a biological signal amplifier electrically coupled to the biological signal measuring unit, for amplifying the biological signal acquired by the biological signal measuring unit;

an A/D converter electrically coupled to the biological signal amplifier, for converting the biological signal to a digital biological signal; and a processor electrically coupled to the A/D converter and the flicker generating unit, the processor is used for:

performing a computation process to the digital biological signal to acquire an average captured reference phase corresponding to the reference phase, of the digital biological signal, and to acquire an average captured shifting phase corresponding to one of the shifting phases, of the digital biological signal; and comparing frequencies and phase states of the digital biological signal and the flickering sequences to output the corresponding control signal.

10. The visual drive control apparatus with multi-phase encoding of claim 8, wherein the optical images are formed by a pure light or an adjustable brightness pattern respectively.

11. The visual drive control apparatus with multi-phase encoding of claim 8, wherein the display unit has a plurality of optical devices, the optical devices have fixed or adjustable flicker cycles.

12. The visual drive control apparatus with multi-phase encoding of claim 8, wherein the flickering sequences are generated by a programmable chip comprising single chip processor, FPGA or micro-controller.

13. The visual drive control apparatus with multi-phase encoding of claim 8, wherein the biological signal measuring unit is used for acquiring the biological signal of the organism by attaching at least one electrode on the brain visual area, attaching a reference electrode on the post auricular mastoid and attaching a ground electrode on the forehead of the organism in accordance with standard 10-20 system.

14. The visual drive control apparatus with multi-phase encoding of claim 8, further comprising a control unit electrically coupled to the signal processing unit, for receiving the control signal to control peripheral equipments and to perform a corresponding action.

* * * * *